(12) United States Patent
Dyballa et al.

(10) Patent No.: US 10,093,690 B2
(45) Date of Patent: Oct. 9, 2018

(54) HETEROCYCLIC SELENAPHOSPHITES AND PROCESS FOR PREPARATION THEREOF

(71) Applicant: EVONIK DEGUSSA GMBH, Essen (DE)

(72) Inventors: Katrin Marie Dyballa, Recklinghausen (DE); Robert Franke, Marl (DE); Claudia Weilbeer, Bernburg (DE); Detlef Selent, Rostock (DE); Armin Börner, Rostock (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/370,472

(22) Filed: Dec. 6, 2016

(65) Prior Publication Data

US 2017/0158721 A1 Jun. 8, 2017

(30) Foreign Application Priority Data

Dec. 7, 2015 (EP) .................................... 15198153

(51) Int. Cl.
| | |
|---|---|
| *C07F 9/547* | (2006.01) |
| *C07C 29/00* | (2006.01) |
| *C07C 37/00* | (2006.01) |
| *C07F 9/6574* | (2006.01) |

(52) U.S. Cl.
CPC .............. *C07F 9/547* (2013.01); *C07C 29/00* (2013.01); *C07C 37/00* (2013.01); *C07F 9/65744* (2013.01)

(58) Field of Classification Search
None
See application file for complete search history.

(56) References Cited

U.S. PATENT DOCUMENTS

| 2015/0336885 A1 | 11/2015 | Dyballa et al. |
| 2016/0010225 A1 | 1/2016 | Dyballa et al. |
| 2016/0010226 A1 | 1/2016 | Dyballa et al. |

FOREIGN PATENT DOCUMENTS

| DE | 102013203865 A1 | 9/2014 |
| DE | 102013203867 A1 | 9/2014 |
| EP | 2949646 A1 | 12/2015 |

OTHER PUBLICATIONS

Chemical Abstract Registry No. 859821-79-7, indexed in the Registry File on STN CAS Online Aug. 12. 2005.*
International Search Report for EP 15 19 8153 dated May 19, 2016 (1 page).
Li, J. L. et al. Synthesis of phosphorus- and selenium-containing macrocycles and their complexation with Pd (II) Cl2. Journal of The Chemical Society, Perkin Transactions 1, (9), 2001, 1140-1146.
Franke, R., Selent, D., and Börner, A. Applied Hydroformylation. American Chemical Society, ACS Publications, Chemical Reviews, 2012. 5675-5732.
Tricas, Hugo, et, al, Bulky monophosphite ligands for ethene hydroformylation, J. of Catalysis, 2012, 198-205.
Paine, Tapan Kanti, et al. Manganese complexes of mixed O, X, O CHEN, -donor ligands (X=S or Se): synthesis, characterization and catalytic reactivity. Dalton Trans. 2003, 3136-3144.
Kamer, Paul C. J. et. al. Phosphorus (III) Ligands in Homogeneous Catalysis: Design and Synthesis. John Wiley and Sons, LTD. 2012, 94-131.
Lin, He M., et. al. A novel and efficient synthesis of selenides. Arkivoc, 2012, 146-156.

* cited by examiner

*Primary Examiner* — Po-Chih Chen
(74) *Attorney, Agent, or Firm* — Smith, Gambrell & Russell, LLP

(57) ABSTRACT

Novel heterocyclic selenaphosphites, process for preparation thereof and use thereof as ligand for employment in complexes.

17 Claims, No Drawings

HETEROCYCLIC SELENAPHOSPHITES AND PROCESS FOR PREPARATION THEREOF

Novel heterocyclic selenaphosphites, process for preparation thereof and use thereof as ligand for employment in complexes.

T. K. Paine describes a synthesis of 2,2'-selenobis(4,6-di-tert-butylphenol) using selenium dioxide. The preparation of 2,2'-selenobis(4,6-di-tert-butylphenol) is effected here in an acidic medium with addition of concentrated hydrochloric acid, The product is obtained with a yield of 25% (T. K. Paine et al., "Manganese complexes of mixed O, X, O-donor ligands (X=S or Se): synthesis, characterization and catalytic reactivity", Dalton Trans., 2003, 15, 3136-3144). It is particularly disadvantageous here that the yields are very low and therefore in need of improvement.

H. M. Lin et al., "A novel and efficient synthesis of selenides", ARKIVOC, 2012, viii, 146-156, discloses another multi-stage synthetic route using Grignard reagents. A synthetic route to selenobiaryl ethers is disclosed in which bromine must be added to the corresponding phenol in order to then convert the product to a Grignard reagent with magnesium. The Grignard reagent can then react with the added selenium before the actual coupling to give the biaryl ether:

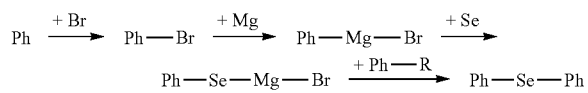

The product was obtained in a good yield, but this synthetic route is very complex, which makes it unattractive for industrial scale use. In this case, a multitude of synthetic steps are needed, the procedure for which is not uncritical in some cases, especially considering scale-up and using standards which are customary in industry. Moreover, this synthetic route gives rise to large amounts of waste products and solvents which have to be disposed of in a costly and inconvenient manner, one reason for which is the use of bromine.

EP 15168645.8 or U.S. Ser. No. 14/720,063 describes a large-scale economic synthetic route for preparing seleno-diphenols.

The reactions between olefin compounds, carbon monoxide and hydrogen in the presence of a catalyst to give the aldehydes comprising one additional carbon atom are known as hydroformylation or oxidation. In these reactions, compounds of the transition metals of group VIII of the Periodic Table of the Elements are frequently employed as catalysts. Known ligands are, for example, compounds from the classes of the phosphines, phosphites and phosphonites, each with trivalent phosphorus $P^{III}$. A good overview of the status of hydroformylation of olefins is found in R. Franke, D. Selent, A. Börner, "Applied Hydroformylation", Chem. Rev., 2012, DOI:10.1021/cr3001803.

Every catalytically active composition has its specific benefits. According to the feedstock and target product, therefore, different catalytically active compositions are used.

Rhodium-monophosphite complexes in catalytically active compositions are suitable for the hydroformylation of branched olefins having internal double bonds. Since the 1970s, there have been descriptions of the use of "bulky phosphites" in hydroformylation (see, inter alfa, van Leeuwen et al., Journal of Catalysis, 2013, 298, 198-205). These feature good activity, but the n/i selectivity for terminally oxidized compounds is low and in need of improvement.

In these hydroformylations, monophosphites and bisphosphites are generally used, which are often formed from biphenol units. The development of novel ligands is frequently limited by the available biphenol, that is, ligand units. For instance, 2,2'-selenobiaryl ethers and also diphenyiseienoxides and diphenylselenides represent a highly interesting class of compound. The 2,2'-selenobiaryl ethers are currently only being used in certain complexes, especially those containing manganese, but they have great potential for further uses.

The object of the invention was to provide a further wholly novel substance class of ligands and ligand units in order to broaden the field of available ligands for the respective specific complexes in catalysis. The object also consisted of producing ligands for rhodium hydroformylation catalysts. The object therefore also consisted of novel intermediates as ligand units for preparing ligands. The objects are achieved with the heterocyclic selenaphosphites according to claim 1, the process according to claim 6 and the use according to claim 14. Particular embodiments are disclosed in the dependent claims and also detailed in the description. The objects are preferably achieved by selenaphosphites of the structures I and Ia, especially with $R^1$ selected from structure I, VII, VIII, IX and X. In the structures, the hydrogen-, alkyl- and —O—$(C_1$-$C_{12})$-alkyl-substituted compounds of $R^1$ in the structures mentioned are particularly preferred compounds.

The invention provides compounds of a heterocyclic selenaphosphite having a general structure I

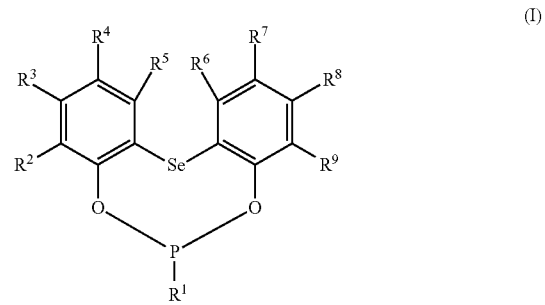

where $R^2$, $R^3$, $R^4$, $R^5$, $R^6$, $R^7$, $R^8$ and $R^9$ are each independently selected from: —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, —OC=O—$(C_1$-$C_{12})$-alkyl, —S-alkyl, —S-aryl, —COO—$(C_1$-$C_{-12})$-alkyl, —CONH—$(C_1$-$C_{12})$-akyl, —CO—$(C_1$-$C_{12})$-alkyl, —CO—$(C_6$-$C_{20})$-aryl, —COOH, —$SO_3H$, —CN, —N[$(C_1$-$C_{12})$-alkyl]$_2$, where the alkyl and aryl groups are each independently unsubstituted or substituted, where each substituted -$(C_1$-$C_{12})$-alkyl group and substituted -$(C_6$-$C_{20})$-aryl group may have at least one substituent and the at least one substituent in each case is independently selected from -$(C_3$-$C_{12})$-cycloalkyl, -$(C_3$-$C_{12})$-heterocycloalkyl, -$(C_6$-$C_{20})$-aryl, fluorine, chlorine, cyano, formyl, acyl or alkoxycarbonyl, and where —$R^1$ is independently selected from —O—$(C_6$-$C_{20})$-aryl, —O—$(C_6$-$C_{20})$-aryl-$(C_1$-$C_{12})$-alkyl, —O—$(C_6$-$C_{20})$-aryl-O—$(C_1$-$C_{12})$-alkyl, —O—$(C_6$-$C_{20})$-aryl-$(C_6$-$C_{20})$-aryl, —O—$(C_6$-$C_{20})$-aryl-O—$(C_6$-$C_{20})$-aryl, —O—$(C_1$-$C_{12})$-alkyl-O—$(C_1$-$C_{12})$-alkyl, —O—$(C_1$-$C_{12})$-alkyl-$(C_6$-$C_{20})$-aryl, —O—$(C_3$-$0_{12})$-cyclcalkyl, where alkyl in each case is independently linear, branched or cyclic, where the alkyl and aryl groups mentioned are each independently unsubstituted or substituted, each substituted —(C$_6$-C$_{20}$)-aryl group has at least one or more than one substituent;

where the substituents on each aryl group may independently be selected from: —O—(C$_1$-C$_{12}$)-alkyl, —(C$_1$-C$_{12}$)-alkyl-O—(C$_1$-C$_{12}$)-alkyl, —(C$_1$-C$_{12}$)-alkyl, —O—(C$_6$-C$_{20}$)-aryl, —O—(C$_1$-C$_{12}$)-alkyl-O—(C$_1$-C$_{12}$)-alkyl, —O—(C$_6$-C$_{20}$)-aryl-O—(C$_1$-C$_{12}$)-alkyl, —(C$_3$-C$_{12}$)-cycloalkyl, —(C$_3$-C$_{12}$)-heterocycloalkyl, —(C$_6$-C$_{20}$)-aryl, cyano, -halogen, —O(C=O)—O—(C$_1$-C$_{12}$)-alkyl, —N[(C$_1$-C$_{12}$)-alkyl]$_2$.

In particularly preferred alternatives, R$^1$ in the structure I may be selected from compounds of the structures II, III, IV, V, VI, VII, VIII, IX and X which follow. R$^1$ in the structure I is an —O-bridged organofunctional radical. IX is a cyclododecanyl radical and X a menthyl radical.

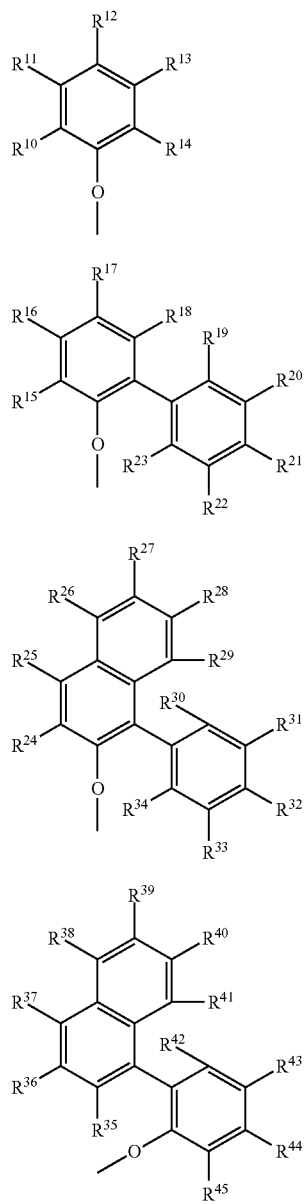

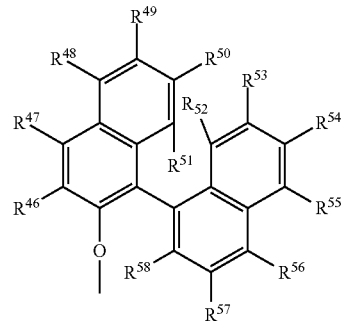

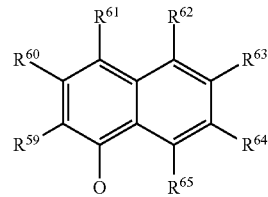

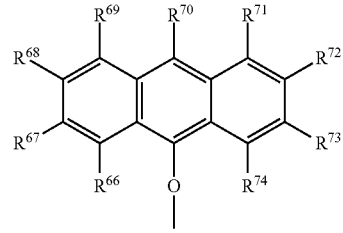

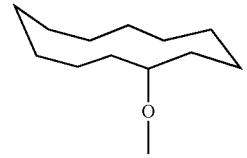

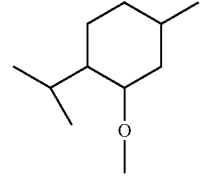

where the radicals

R$^{10}$, R$^{11}$, R$^{12}$, R$^{13}$, R$^{14}$ in the structure II,

R$^{15}$, R$^{16}$, R$^{17}$, R$^{18}$, R$^{19}$, R$^{20}$, R$^{21}$, R$^{22}$ and R$^{23}$ in structure III, R$^{24}$, R$^{25}$, R$^{26}$, R$^{27}$, R$^{28}$, R$^{29}$, R$^{30}$, R$^{31}$, R$^{32}$, R$^{33}$ and R$^{34}$ in structure IV, R$^{35}$, R$^{36}$, R$^{37}$, R$^{38}$, R$^{39}$, R$^{40}$, R$^{41}$, R$^{42}$, R$^{43}$, R$^{44}$ and R$^{45}$ in structure V, R$^{46}$, R$^{47}$, R$^{48}$, R$^{49}$, R$^{50}$, R$^{51}$, R$^{52}$, R$^{53}$, R$^{54}$, R$^{55}$, R$^{56}$, R$^{57}$ and R$^{58}$ in structure VI, R$^{59}$, R$^{60}$, R$^{61}$, R$^{62}$, R$^{63}$, R$^{64}$ and R$^{65}$ in structure VII, and R$^{66}$, R$^{67}$, R$^{68}$, R$^{69}$, R$^{70}$, R$^{71}$, R$^{72}$, R$^{73}$ and R$^{74}$ in structure VIII, in each structure may each independently be selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, where the alkyl and aryl groups may each independently be unsubstituted or substituted, where each substituted —($C_1$-$C_{12}$)-alkyl group and each substituted —($C_6$-$C_{20}$)-aryl group may have at least one substituent and the at least one substituent may in each case independently be selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, where, in the structures III, IV, V and VI, $R^{23}$, $R^{34}$, $R^{45}$, $R^{58}$ may each independently additionally be selected from —O—X with X=protecting group, where the protecting group X may be selected from —(C1-C12)-alkyl, —($C_6$-$C_{20}$)-aryl-O—($C_1$-$C_{12}$)-alkyl, —COO—($C_1$-$C_{12}$)-alkyl.

In a further particularly preferred alternative, the heterocyclic selenaphosphite may have the general structure Ia

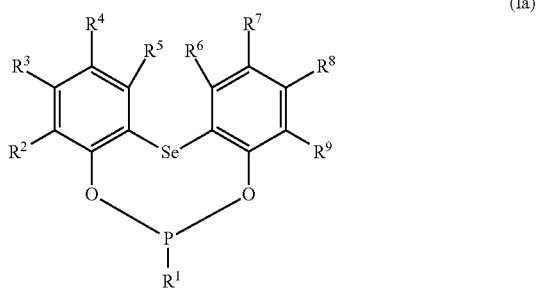

(Ia)

where each of $R^2$, $R^3$, $R^4$, $R^5$, $R^6$, $R^7$, $R^8$ and $R^9$ in the structure Ia is independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, and with —$R^1$ in the heterocyclic selenaphosphite of the general structure Ia independently selected from the structures II, III, IV, V, VI, VII, VIII, IX and X, as illustrated above, where the radicals $R^{10}$, $R^{11}$, $R^{12}$, $R^{13}$, $R^{14}$ in the structure II, $R^{15}$, $R^{16}$, $R^{17}$, $R^{18}$, $R^{19}$, $R^{20}$, $R^{21}$ and $R^{22}$ in structure III, $R^{24}$, $R^{25}$, $R^{26}$, $R^{27}$, $R^{28}$, $R^{29}$, $R^{30}$, $R^{31}$, $R^{32}$ and $R^{33}$ in structure IV, $R^{35}$, $R^{36}$, $R^{37}$, $R^{38}$, $R^{39}$, $R^{40}$, $R^{41}$, $R^{42}$, $R^{43}$ and $R^{44}$ in structure V, and/or $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ in structure VI, $R^{59}$, $R^{60}$, $R^{61}$, $R^{62}$, $R^{63}$, $R^{64}$ and $R^{65}$ in structure VII, and $R^{66}$, $R^{67}$, $R^{68}$, $R^{69}$, $R^{70}$, $R^{71}$, $R^{72}$, $R^{73}$ and $R^{74}$ in structure VIII, may each independently be selected from: —H, —($C_1$-$C_{12}$)-alkyl, —O—($C_1$-$C_{12}$)-alkyl, -halogen, and where, in each case independently, in addition to the aforementioned groups in the structures III, IV, V and VI, $R^{23}$, $R^{34}$, $R^{45}$, $R^{58}$ may each independently be selected from —H, -($C_1$-$C_{12}$)-alkyl, -halogen and —O—X with X=protecting group, where the protecting group X is selected from -($C_1$-$C_{12}$)-alkyl, —($C_1$-$C_{12}$)-alkyl-O—($C_1$-$C_{12}$)-alkyl, —($C_6$-$C_{20}$)-aryl-O—($C_1$-$C_{12}$)-alkyl, —COO—($C_1$-$C_{12}$)-alkyl, In accordance with a further preferred alternative, the heterocyclic selenaphosphite of the general structure Ia may be selected from at least one compound of the structure Ib with $R^1$ corresponding to the definition for the compound of the structure Ia,

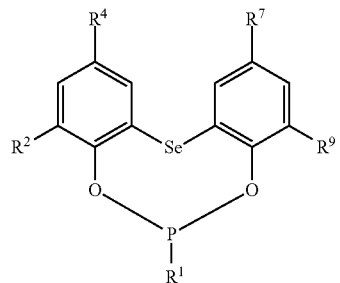

(Ib)

where $R^2$, $R^4$, $R^7$ and $R^9$ may each be independently selected from: —($C_1$-$C_{12}$)-alkyl, —O—($C_1$-$C_{12}$)-alkyl, —($C_6$-$C_{20}$)-aryl, —O—($C_6$-$C_{20}$)-aryl, halogen.

The invention likewise provides the aforementioned structures of the selenaphosphites and selenodiaryls of the structures I and Ia with $R^2$, $R^3$, $R^4$, $R^5$, $R^6$, $R^7$, $R^8$ and $R^9$, each of which may independently selected from: —H, —($C_1$-$C_{12}$)-alkyl, —O—($C_1$-$C_{12}$)-aryl, —($C_6$-$C_{20}$)-aryl,—O—($C_6$-$C_{20}$)-aryl, -halogen, wherein the alkyl and aryl groups are each independently unsubstituted. The alkyl groups are preferably unsubstituted. More preferably, $R^2$, $R^3$, $R^4$, $R^5$, $R^6$, $R^7$, $R^8$ and $R^9$ are each independently selected from methyl, ethyl, tert-butyl, isopentyl, methoxy.

The invention likewise provides the aforementioned structures of the selenaphosphites and selenodiaryls of the structures Ib with $R^2$, $R^4$, $R^7$ and $R^9$, each of which may independently selected from: —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, wherein the alkyl and aryl groups are each independently unsubstituted.

In an alternative, $R^2$, $R^3$, $R^4$, $R^5$, $R^6$, $R^7$, $R^8$ and $R^9$ in a heterocyclic selenaphosphite of the general structure I and Ia are each independently selected from: —H and —($C_1$-$C_{12}$)-alkyl and/or —O—($C_1$-$C_{12}$)-alkyl groups, wherein the alkyl groups may be linear, branched or cyclic. The alkyl groups are preferably unsubstituted.

In an alternative, $R^2$, $R^4$, $R^7$ and $R^9$ in a heterocyclic selenaphosphite of the general structure Ib are each independently selected from:

—($C_1$-$C_{12}$)-alkyl and/or —O—($C_1$-$C_{12}$)-alkyi groups, where the alkyl groups may be linear, branched or cyclic. The alkyl groups are preferably unsubstituted. Particular preference is given to $R^2$, $R^4$, $R^7$, $R^9$, each of which may be methyl, ethyl, tert-butyl, isopentyl, methoxy.

For the heterocyclic selenaphosphites of the aforementioned general structure Ia or Ib, it is further preferred when $R^1$ may correspond to one of the structures selected from II, III, IV, V, VI, VIII, IX and X, particular preference being given to the structures II, III, and radicals in the structures being selected from:

$R^{10}$, $R^{11}$, $R^{12}$, $R^{13}$, $R^{14}$ in the structure II, $R^{15}$, $R^{16}$, $R^{17}$, $R^{18}$, $R^{19}$, $R^{20}$, $R^{21}$, $R^{22}$ and $R^{23}$ in structure III, $R^{24}$, $R^{25}$, $R^{26}$, $R^{27}$, $R^{28}$, $R^{29}$, $R^{30}$, $R^{31}$, $R^{32}$, $R^{33}$ and $R^{34}$ in structure IV, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ in structure V, and/or $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$ and $R^{58}$ in structure VI, $R^{59}$, $R^{60}$, $R^{61}$, $R^{62}$, $R^{63}$, $R^{64}$ and $R^{65}$ in structure VII, and $R^{66}$, $R^{67}$, $R^{68}$, $R^{69}$, $R^{70}$, $R^{71}$, $R^{72}$, $R^{73}$ and $R^{74}$ in structure VIII, in each structure may each independently be selected from: —H, —$(C_1$-$C_{12})$-alkyl, -halogen, where the alkyl groups may each independently be substituted, where, in the structures III, IV, V and VI, $R^{23}$, $R^{34}$, $R^{45}$, $R^{58}$ may each independently be selected from —H, —$(C_1$-$C_{12})$-alkyl, —O—X with X=protecting group, where the protecting group X may be selected from —$(C_1$-$C_{12})$-akyl, —$(C_6$-$C_{20})$-aryl-O—$(C_1$-$C_{12})$-alkyl, —COO—$(C_1$-$C_{12})$-alkyl.

In structure II, $R^{10}$ and $R^{12}$ are preferably selected from tert-butyl, methyl, ethyl, isopropyl, isopentyl, and $R^{11}$, $R^{13}$, $R^{14}$ are —H.

Likewise claimed is at least one heterocyclic selenaphosphite of the general structure I, where $R^2$, $R^3$, $R^4$, $R^5$, $R^6$, $R^7$, $R^8$ and $R^9$ are each independently selected from: —H, —$(C_1$-$C_{12})$-alkyl, —O—$(C_1$-$C_{12})$-alkyl, and —$R^1$ in the heterocyclic selenaphosphite of the general structure I is independently selected from the structures II, III, IV, V, VI, VII, VIII, IX and X, where the aforementioned radicals are each independently selected from: —H, —$(C_1$-$C_{12})$-alkyl, —O—$(C_1$-$C_{12})$-alkyl, and where, in each case independently, in addition to the aforementioned radicals in the structures III, IV, V and VI, $R^{23}$, $R^{34}$, $R^{45}$, $R^{58}$ are each independently selected from —H, —$(C_1$-$C_{12})$-alkyl, and —O—X with X=protecting group, where the protecting group X is selected from —$(C_1$-$C_{12})$-alkyl, —$(C^6 C_{20})$-aryl, —$(C_1$-$C_{12})$-alkyl-O—$(C_1$-$C_{12})$-alkyl, —$(C_6$-$C_2)$-aryl-O—$(C_1$-$C_{12})$-alkyl.

Likewise claimed is at least one heterocyclic selenaphosphite of the general structure I, where $R^2$, $R^3$, $R^4$, $R^5$, $R^6$, $R^7$, $R^8$ and $R^9$ are each independently selected from: —H, —$(C_1$-$C_{12})$-alkyl, —O—$(C_1$-$C_{12})$-alkyl, and —$R^1$ in the heterocyclic selenaphosphite of the general structure I is independently selected from the structures II, VII, VIII, where the radicals in II, VII, VIII are each independently selected from: —H, —$(C_1$-$C_{12})$-alkyl, —O—$(C_1$-$C_{12})$-alkyl.

Likewise claimed is at least one heterocyclic selenaphosphite of the general structure I, where $R^2$, $R^3$, $R^4$, $R^5$, $R^6$, $R^7$, $R^8$ and $R^9$ are each independently selected from: —H, —$(C_1$-$C_{12})$-alkyl, and —$R^1$ in the heterocyclic selenaphosphite of the general structure I is independently selected from the structure II, where the radicals in II are each independently selected from: —H, —$(C_1$-$C_{12})$-alkyl.

Likewise claimed is at least one heterocyclic selenaphosphite of the general structure I, where $R^2$, $R^3$, $R^4$, $R^5$, $R^6$, $R^7$, $R^8$ and $R^9$ are each independently selected from: —H, —$(C_1$-$C_{12})$-alkyl, —O—$(C_1$-$C_{12})$-alkyl, and —$R^1$ in the heterocyclic selenaphosphite of the general structure I is independently selected from the structures IX and X.

Particular preference is given to a heterocyclic selenaphosphite of the general structure Ib where $R^2$, $R^4$, $R^7$ and $R^8$ are each methyl and —$R^1$ corresponds to the single-crystal structure H with $R^{10}$, $R^{12}$=methyl and $R^{11}$, $R^{13}$ and $R^{14}$=—H.

The invention further provides a process for preparing at least one heterocyclic selenaphosphite of the general structure I according to the above definition, and the selenaphosphites obtainable by the process.

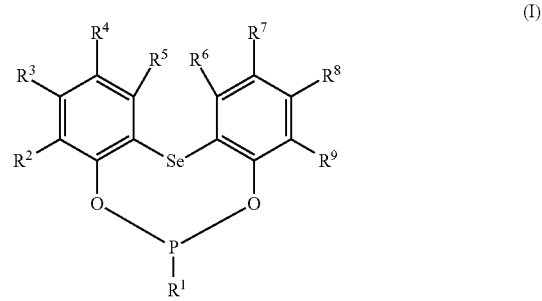

(I)

where $R^2$, $R^3$, $R^4$, $R^5$, $R^6$, $R^7$, $R^8$ and $R^9$ are each independently selected from: —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, —OC=O—$(C_1$-$C_{12})$-alkyl, —S-alkyl, —S-aryl, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —$SO_3H$, —CN, —N[$(C_1$-$C_{12})$-alkyl]$_2$, where the alkyl and aryl groups are each independently unsubstituted or substituted, where the respective substituted —$(C_1$-$C_{12})$-alkyl group and substituted —$(C_6$-$C_{20})$-aryl group has at least one substituent and the at least one substituent in each case is independently selected from —$(C_3$-$C_2)$-cycloalkyl, —$(C_3$-$C_{12})$-heterocycloalkyl, —$(C_6$-$C_{20})$-aryl, fluorine, chlorine, cyano, formyl, acyl or alkoxycarbonyl, and where —$R^1$ may independently be selected from —O—$(C_6$-$C_{20})$-aryl, —O—$(C_6$-$C_{20})$-aryl-$(C_1$-$C_{12})$-alkyl, —O—$(C_6$-$C_{20})$-aryl-O—$(C_1$-$C_{12})$-alkyl, —O—$(C_6$-$C_{20})$-aryl-$(C_6$-$C_{20})$-aryl, —O—$(C_6$-$C_{20})$-aryl-O—$(C_6$-$C_{20})$-aryl, —O—$(C_1$-$C_{12})$-alkyl, —O—$(C_1$-$C_{12})$-alkyl-O—$(C_1$-$C_{12})$-alkyl, —O—$(C_1$-$C_{12})$-alkyl-$(C_5$-$C_{20})$-aryl, —O—$(C_3$-$C_{12})$-cycloalkyl, where alkyl may in each case independently be linear, branched or cyclic, where the alkyl and aryl groups mentioned may each independently be unsubstituted or substituted, each substituted —$(C_6$-$C_{20})$-aryl group may have at least one or more than one substituent;

where the substituents on each aryl group may independently be selected from: —O—$(C_1$-$C_{12})$-alkyl, —$(C_{,1}$-$C_{12})$-alkyl-O-$(C_1$-$C_{12})$-aryl, —$(C_1$-$C_{12})$-alkyl, —O—$(C_6$-$C_{20})$-aryl, —O—$(C_1$-$C_{12})$-alkyl-O—$(C_1$-$C_{12})$-alkyl, —O—$(C_6$-$C_{20})$-aryl-O—$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, cyano, -halogen, —OCOO—$(C_1$-$C_{12})$-alkyl, —N[$(C_1$-$C_{12})$-alky]$_2$.

comprising at least the process step of
(i) reacting a selenodiaryl of the general structure XI

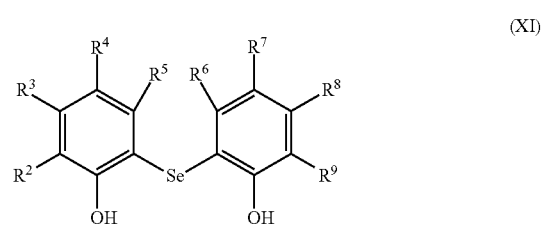

(XI)

where $R^2$, $R^3$, $R^4$, $R^5$, $R^6$, $R^7$, $R^8$ and $R^9$ are each independently selected from: —H, —$(C_1$-$C_{12})$-alkyl, —O—$(C_1$-$C_{12})$-alkyl, —$(C_6$-$C_{20})$-aryl, —O—$(C_6$-

$C_{20}$)-aryl, -halogen, —OC=O—($C_1$-$C_{12}$)alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3H$, —CN, —N[($C_1$-$C_{12}$)-alkyl]$_2$, where the alkyl and aryl groups are each independently unsubstituted or substituted, where each substituted —($C_1$-$C_{12}$)-alkyl group and substituted —($C_6$-$C_{20}$)-aryl group may have at least one substituent and the at least one substituent in each case is independently selected from -($C_3$-$0_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, especially as defined above for structure I, (ii) with a dihalophosphite compound $R^1P(Hal)_2$ of the formula XII where Hal is selected from fluorine, chlorine, bromine, iodine, preference being given to chlorine and bromine, particular preference to chlorine, where $R^1$ may correspond to the aforementioned definition, particular preference being given to reaction with a compound of the formula XII selected from $R^1PCl_2$ and $R^1PBr_2$, (iii) and obtaining at least one selenaphosphite of the general structure I.

In accordance with a preferred embodiment of the process, it is possible to use a selenodiaryl of the general structure XIa

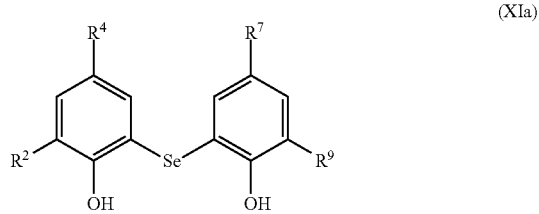

(XIa)

where $R^2$, $R^4$, $R^7$ and $R^9$ are each independently selected from: —($C_1$-$C_{12}$)-alkyl, —O—($C_1$-$C_{12}$)-alkyl, —($C_6$-$C_{20}$)-aryl, —O—($C_5$-$C_{20}$)-aryl, -halogen.

In addition, it is preferable when, in the process, the compound reacted with the selenodiaryl of the structure XI or XIa is a dihalophosphite compound of the formula $R^1P(Hal)_2$ of the formula XII with Hal selected from fluorine, chlorine, bromine, iodine, especially chlorine and bromine, particular preference being given to chlorine, in which $R^1$ may independently be selected from the structures II, III, IV, V, VI, VII, VIII, IX and X as defined above, where the radicals $R^{10}$, $R^{11}$, $R^{12}$, $R^{13}$, $R^{14}$ in the structure II,
$R^{15}$, $R^{16}$, $R^{17}$, $R^{18}$, $R^{19}$, $R^{20}$, $R^{21}$ and $R^{22}$ in structure III,
$R^{24}$, $R^{25}$, $R^{26}$, $R^{27}$, $R^{28}$, $R^{29}$, $R^{30}$, $R^{31}$, $R^{32}$ and $R^{33}$ in structure IV,
$R^{35}$, $R^{36}$, $R^{37}$, $R^{38}$, $R^{39}$, $R^{40}$, $R^{41}$, $R^{42}$, $R^{43}$ and $R^{44}$ in structure V,
$R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ in structure VI,
$R^{59}$, $R^{60}$, $R^{61}$, $R^{62}$, $R^{63}$, $R^{64}$ and $R^{65}$ in structure VII, and $R^{66}$, $R^{67}$, $R^{68}$, $R^{69}$, $R^{70}$, $R^{71}$, $R^{72}$, $R^{73}$ and $R^{74}$ in structure VIII, in each structure are each independently selected from: —H, —($C_1$-$C_{12}$)-alkyl, —O—($C_1$-$C_{12}$)-alkyl, -halogen, and where, in each case independently, in addition to the aforementioned groups in the structures III, IV, V and VI, $R^{23}$, $R^{34}$, $R^{45}$, $R^{56}$ are each independently selected from —H, —($C_1$-$C_{12}$)-alkyl, -halogen and —O—X with X=protecting group, where the protecting group X is selected from —($C_1$-$C_{12}$)-alkyl, —($C_1$-$C_{12}$)-alkyl-O—($C_1$-$C_{12}$)-alkyl, —($C_6$-$C_{20}$)-aryl-O—($C_1$-$C_{12}$)-alkyl, —COO-($C_1$-$C_{12}$)-alkyl.

According to the invention, the dihalophosphite compound $R^1P(Hal)_2$ is an organofunctional dihalophosphite compound.

The (i) reaction in the process according to the invention is effected in the presence of a base, especially of an amine or a pyridine base, especially an alkylamine such as triethylamine or dimethylaminobutane, especially triethylamine.

In addition, the (i) reaction is effected by reacting the selenodiaryl of the general structure XI with $R^1P(Hal)_2$ of the formula XII in a molar ratio of 10:1 to 1:10, preferably in a ratio of 2:1 to 1:2, more preferably 1.5:1 to 1:1.5.

In addition, the (i) reaction is preferably effected at a temperature of —45 to 80° C., particularly of –15 to 30° C., especially of –5 to 5° C.

The invention likewise provides for the use of a heterocyclic selenaphosphite of the structure I, Ia and Ib or of the composition comprising at least one selenaphosphite of the structure I obtainable by the process as ligand.

The terms "phenol", "aryl" and "phosphite" are used as generic terms in this application and therefore also encompass substituted structures of the compounds mentioned.

One or more substituents in the aforementioned structures of the selenaphosphites and selenodiaryls comprise preferably 1 to 10 substituents, in particular 1 to 3.

In the context of the invention, the expression "-($C_1$-$C_{12}$)-alkyl" encompasses straight-chain and branched alkyl groups. Preferably, these groups are unsubstituted straight-chain or branched —($C_1$-$C_8$)-alkyl groups and most preferably —($C_1$-$C_6$)-alkyl groups. Examples of —($C_1$-$C_{12}$)-alkyl groups are particularly methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

Halogen as substituent on alkyl or aryl includes fluorine, chlorine, bromine and iodine, particular preference being given to chlorine and fluorine.

All elucidations relating to the expression —($C_1$-$C_{12}$)-alkyl in the aforementioned structures of the selenaphosphites and selenodiaryls according to the invention also apply to the alkyl groups in —O—($C_1$-$C_{12}$)-alkyl, that is, in —($C_1$-$C_{12}$)-alkoxy.

25

Preference is given to unsubstituted straight-chain or branched —($C_1$-$C_6$)-alkoxy groups, Substituted —($C_1$-$C_{12}$)-alkyl groups and substituted —($C_1$-$C_{12}$)-alkoxy groups in the aforementioned structures of the selenaphosphites and selenodiaryls may have one or more substituents, depending on their chain length. The substituents are preferably each independently selected from: —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl orzr alkoxycarbonyl. This definition applies to all substituted alkyl or alkoxy groups of the present invention.

All elucidations relating to the expression —($C_6$-$C_{20}$)-aryl in the aforementioned structures of the selenaphosphites and seienodiaryis according to the invention also apply to the aryl groups in —O—($C_6$-$C_{20}$)-aryl.

Preference is given to unsubstituted —O—($C_6$-$C_{20}$)-groups.

In the context of the present invention, the expression "—($C_6$-$C_{20}$)-aryl and -($C_6$-$C_{20}$)-aryl-($C_6$-$C_{20}$)-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —($C_6$-$C_{10}$)-aryl and —($C_6$-$C_{10}$)-aryl-($C_8$-$C_{10}$)-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

The expression "—($C_3$-$C_{12}$)-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl or adamantyl.

One example of a substituted cycloalkyl would be menthyl.

The expression "—($C_3$-$C_{12}$)-heterocycloalkyl groups", in the context of the present invention, encompasses nonaromatic, saturated or partly unsaturated cycloaliphatic groups having 3 to 12, especially 5 to 12, carbon atoms. The —($C_3$-$C_{12}$)-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— or —S(=O)—, Examples of —($C_3$-$C_{12}$)-heterocycloalkyl groups are tetrahydrothiophenyl, tetrahydrofuryl, tetrahydropyranyl and dioxanyl.

The invention is further illustrated in detail below by examples without the invention being limited to the working examples.

General Methods
Solvents and Reagents

All reactions with moisture- and/or oxygen-sensitive substances were carried out in baked-out apparatuses under an argon atmosphere. Solvents for extraction and column chromatography were used at the following purities: dichloromethane (99.9%, Walter, Cat. No. BIE 073107033) ethyl acetate (99.5%, Walter, Cat. No. BIE 003917025) and n-hexane (95%, Walter (Baker), Cat. No. 8669), n-heptane (95%, Walter (Baked, Cat. No. 8662). Other solvents for extraction and column chromatography were of technical quality and were used without further purification unless otherwise stated. Dry solvents (abs.) were purified using a Pure Solv MD-7 System and stored under an argon atmosphere. Benzyl bromide was freshly distilled (17 mbar/82° C.) prior to use. Deuterated solvents were distilled from the drying agents specified: dichloromethane-$d_2$ (phosphorus pentoxide), toluene-$d_8$ (1. KOH; 2. sodium). Chemicals used for the syntheses were supplied by Sigma Aldrich, Alfa Aesar, Acres Organics, Avantor Performance Materials B. V., Merck KGaA and ABCR GmbH & Co. KG. These were used without further purification unless otherwise stated.

Filtration: Filtrations for the removal of resulting solids were carried out using a G4 frit (pore width: 10-16 μm).

Analysis

IR spectroscopy: IR spectra were recorded with a Nicolet 6700 FT-IR spectrometer from Thermo Electron. The substances were measured by ATR methods.

$^1$H-NMR spectroscopy: $^1$H-NMR spectra were recorded with a model AV 300 (300 MHz) and with the model Fourier 300 (300 MHz) from Bruker, Chemical shifts are stated in units on the δ-scale. The residual proton signals of the solvent (dichloromethane-$d_2$: δ=5.32 ppm, toluene-$d_8$: δ=7.09; 7.00; 6.98; 2.09 ppm) served as standard.

$^{13}$C-NMR spectroscopy: $^{13}$C-NMR spectra were recorded with models AV 300 (75 MHz) and Fourier 300 (75 MHz) from Bruker. The signal of the solvent (dichioromethane-$d_2$: δ=54.0 ppm, toluene-$d_8$:
δ=137.9; 129.2; 128.3; 125.5; 20.4 ppm) served as internal standard wherein the chemical shifts were taken from the broadband $^1$H-decoupled spectra.

$^{77}$Se-NMR spectroscopy: $^{77}$Se-NMR spectra were recorded with an AV 300 (57 MHz) from Bruker. The spectra were measured in broadband $^1$H-decoupled mode. The chemical shifts are reported in ppm.

Mass spectrometry: El mass spectra were recorded on a Finnigan MAT 95-XP instrument from Thermo Electron and ESI-TCF mass spectra with a model 6210 Time-of-Flight LC/MS from Agilent.

SYNTHESIS OF THE PRECURSORS

General Procedure 8.2 mmol of the particular phenol are dissolved in the appropriate solvent (8.2 m). The reaction mixture is heated, and 4.9 mmol of selenium dioxide are added while stirring. The solvent is distilled under reduced pressure (temperature <70° C.), A frit is prepared with 2.5 cm of silica gel (at the bottom) and 2.5 cm of zeolite (at the top). The distillation residue is taken up in the eluent and applied to the filtration column. Cyciohexane:ethyl acetate (95:5) is used to wash the product off the frit and collect it in fractions. The fractions containing the product are combined and freed of the eluent by distillation.

The fractions obtained are recrystallized from 95:5 cyclohexane:ethyl acetate. For this purpose, the solid residue is dissolved at 50° C., and insoluble residues are filtered off using a glass frit. The reaction product crystallizes out of the saturated solution at room temperature overnight. The resulting crystals are washed once again with cold cyclohexane.

The structural formula shows the main product obtained in each reaction.

Bis(3,5-dimethyl-2-hydroxyphenyl)selenium;
structure XI, 1a

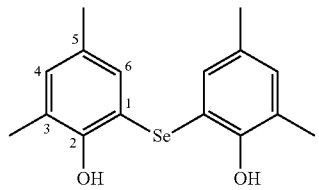

The reaction is conducted according to the general procedure in a screw-top test tube. For this purpose, 1.00 g (8.2 mmol, 1.0 equiv.) of
2,4-dimethylphenol and 0.54 g (4.9 mmol, 0.6 equiv.) of selenium dioxide are dissolved and heated in 1 ml of pyridine. The product is obtained as a colourless crystalline solid.

$^1$H-NMR (400 MHz, CDCl$_3$): δ (ppm)=7.12 (s,2H, 6-H), 6.91 (s, 2H, 4-H), 5.97 (s,2H, OH), 2.23 (s, 6H, 3-CH$_3$) 2.23 (s, 6H, 5-CH$_3$); $^{13}$C-NMR (100 MHz, CDCl$_3$): δ (ppm) =151.7 (C-2),133.2 (C-3), 133.1 (C-5), 130.4 (C-4), 124.2 (C-6), 114.9 (C-1), 20.3 (5-CH$_3$), 16.5 (3-CH$_3$); $^{77}$Se-HMR (76 MHz, CDCl$_3$): δ (ppm)=163.36 ppm.

Bis(3-tert-butly-5-methyl-2-hydroxyphenyl)selenium, structure XI, 1b

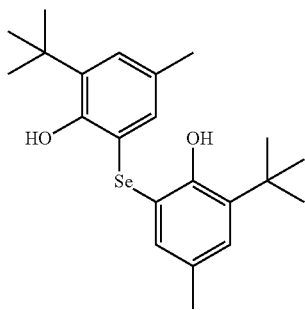 [SMILES: Cc1cc([Se]c2cc(C)cc(C(C)(C)C)c2O)c(O)c(C(C)(C)C)c1]

The reaction is conducted according to the general procedure in a screw-top test tube. For that purpose, 1.32 g (8.0 mmol, 1.0 equiv.) of 2-tert-butyl-4-methylphenol and 0.54 g (4.9 mmol, 0.6 equiv.) of selenium dioxide were dissolved and heated in 1 ml of pyridine.

$^1$H-NMR (300 MHz, CDCl$_3$): δ (ppm)=7.15 (s, 2H, 6-H), 7.05 (s, 2H, 4-H), 5.07 (s,2H, OH), 2.21 (s, 6H, 5-CH$_3$), 2.21 (s, 18H, 3-C(CH$_3$)$_3$: $^{13}$C-NMR (75 MHz, CDCl$_3$): δ (ppm) =152.1, 136.4, 133.4, 120.1, 129.5, 117.2, 35.1, 29.6, 20.8.

3,3', 5,5'-Tetra-tert-butylbiphenyl-2,2'-diol, structure XI, 1c

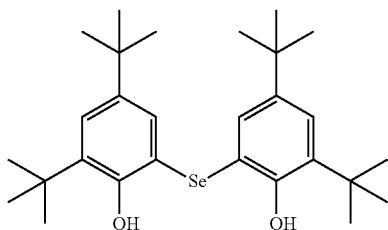 [SMILES: CC(C)(C)c1cc([Se]c2cc(C(C)(C)C)cc(C(C)(C)C)c2O)c(O)c(C(C)(C)C)c1]

The reaction is conducted according to the general procedure in a screw-top test tube. For that purpose, 1.67 g (8.2 mmol, 1.0 equiv.) of 2,4-di-tert-butylphenol and 0.55 g (4.9 mmol, 0.6 equiv.) of selenium dioxide were dissolved and heated in 1 ml of pyridine.

$^1$H-NMR (400 MHz, CDCl$_3$): δ (ppm)=7.31 (d, J=2.4 Hz, 2H), 7.29 (d, J=2.4), 6.29 (s, 2H), 1.42 (s, 18H), 1.24 (s, 18H); $^{13}$C-NMR (75 MHz, CDCl$_3$); δ (ppm)=151.7, 143.5, 135.8, 129.8, 126.6, 117.2, 35,4, 34.4, 31.6, 29.7.

Biphenols

The biphenols are synthesized analogously to DE102013203865 and DE102013203867.

Synthesis of the Chlorophosphites

The synthesis of the dichlorophosphites, such as dichloro ((-)-menthyloxy)phosphite, is known to those skilled in the art and is effected in the manner known per se. Chlorophosphites can be prepared from the corresponding monohydroxyl compounds by addition of phosphorus trichloride in the presence of a base. For further information see also "Phosphorus(III) Ligands in Homogeneous Catalysis—Design and Synthesis" by Paul C. J. Kamer and Piet W. N. M. van Leeuwen; John Wiley and Sons, 2012; including p. 94 ff. and references cited therein.

Synthesis of dichloro(2,4-di-tert-butylphenoxy)phosphite, structure XII, 2a

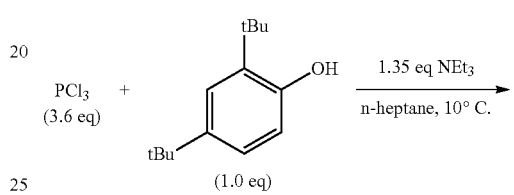

A baked-out 50 ml Schlenk flask under an argon atmosphere was initially charged with 629 μl (989 mg, 7.20 mmol, 3.6 eq) of phosphorus trichloride in 20 ml cf abs. n-heptane and cooled to 10° C. In a separate 10 ml Schlenk flask, 374 μl (273 mg, 2.70 mmol, 1.35 eq) of triethylamine and 412 mg (2.00 mmol, 1.0 eq) of 2,4-di-tert-butylphenol were dissolved in 10 ml of n-heptane and added dropwise to the initial charge of PCl$_3$ over a period of 90 minutes. The latter was rinsed in with 2.0 ml of abs. n-heptane and stirred at RT for 19 h. Subsequently, the reaction mixture was filtered for complete removal of the precipitate formed and the solids were washed with 10 ml of abs. n-heptane. The solvent of the pale yellow solution was removed under reduced pressure and the crude product was dried under vacuum at 50° C. for three hours. 569 mg (1.86 mmol, 93%, 96% pure) of the title compound 2a were obtained as colourless oil.

IR (ATR): v̂(cm$^{-1}$)=2958; 2869; 1494; 1398; 1362; 1302; 1210; 1154; 1085; 982; 939; 887; 823; 783; 745; 699; 645; 598; 509; $^{31}$P-NMR (122 MHz, Toluene-d$_8$): δ (ppm)= 186.0. MS (El): m/z (%)=306 (10.4) [C$_{14}$H$_{21}$Cl$_2$OP]; 291 (100) [C$_{13}$H$_{18}$,Cl$_2$OP]; 271 (2.06) [C$_{14}$H$_{21}$ClOP]; HR-MS (El): calc'd for C$_{14}$H$_{21}$ClOP: 306.07016, found: 306.06994; calc'd for C$_{14}$H$_{21}$ $^{37}$ClOP: 308.06721, found: 308.06731; C$_{14}$H$_{21}$Cl$_2$OP (306.07 g/mol).

Reaction of tert-butyl (3,3'-di-tert-butyl-2'hydroxy-5,5'-dimethoxy-[1,1'-biphenyl -2-yl])carbonate with phosphorus trichloride:

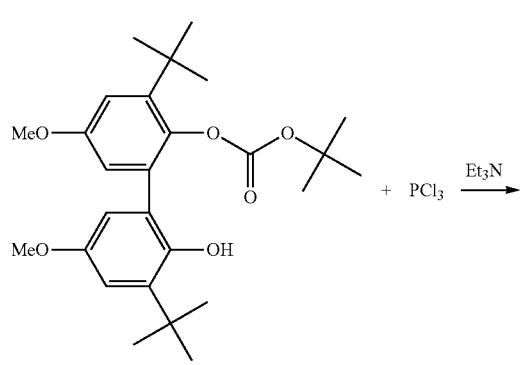

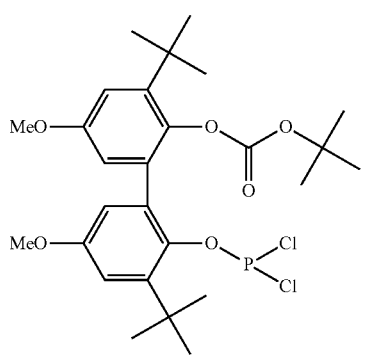

In a 250 ml Schlenk flask which had been repeatedly evacuated and filled with inert gas, 12 g (0.026 mol) of tert-butyl (3,3'-di-tert-butyl-2'-hydroxy-5,5'-dimethoxy-[1,1'-biphenyl]-2-yl)carbonate were dissolved by stirring in 120 ml of dried toluene and 12.8 ml (0.091 mol) of triethylamine.

In a second 500 ml Schlenk flask, 100 ml of dried toluene were first stirred together with 8.1 ml (0.091 mol) of phosphorus trichloride. Subsequently, the phosphorus trichloride-toluene solution was added dropwise to the previously prepared carbonate-amine-toluene solution at room temperature within 30 minutes. On completion of addition, the mixture was heated to 80° C. for 30 minutes and cooled to room temperature overnight. The next morning, the mixture was filtered, the solids were washed with 50 ml of dried toluene, and the filtrate was concentrated to dryness. The target product was obtained as a solid (13.1 g, 89%).
$^{31}$P-NMR (202.4 MHz, toluene-$d_8$): 203.2 and 203.3 ppm.

Preparation of biphenyl-3,3', 5,5'-tetra-tert-butyl-2-hydroxy-2'-dichlorophosphite

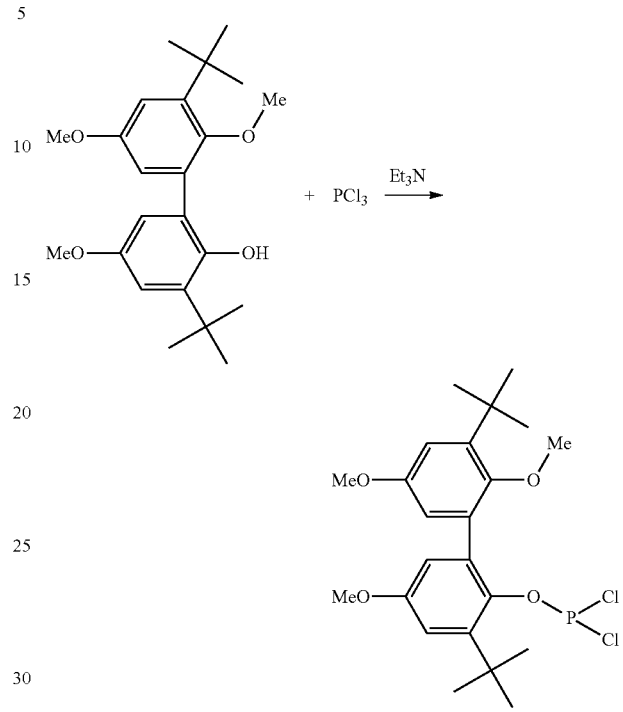

In a 250 ml Schlenk flask which had been repeatedly evacuated and filled with inert gas, 10.62 g (0.025 mol) of 3,3',5,5'-tetra-tert-butyl-2-hydroxy-2'-rnethoxybiphenyl were dissolved with stirring in 50 ml of dried toluene and admixed with 3.5 ml (0.025 mol) of triethylamine. Added dropwise to the resulting solution, at room temperature and with vigorous stirring, are 2.2 ml (0.025 mol) of phosphorus trichloride, and the mixture is then heated at 105° C. for 4 hours. It is worked up by filtering off the precipitated ammonium chloride and washing the filter product 2 times with 25 ml of toluene. The filtrate is concentrated to dryness. The product was obtained in 63% yield.

Analogously to the preparation of the dichloro(2,4-di-tert-butylphenoxy)phosphite, it is correspondingly possible to prepare phenols, 1-naphthols, 2-naphthols, anthracene derivatives such as 9-hydroxyanthracene, and cycloalkanol compounds.

The Synthesis of the Selenium Phosphites

Synthesis of 6-(2,4-di-tert-butylphenoxy)-2,4,8,10-tetramethyldibenzo[d,c][1,3,6,2]dioxaselenaphol-sphocine, structure I; 3a

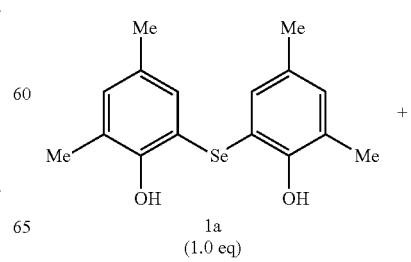

1a
(1.0 eq)

17

-continued

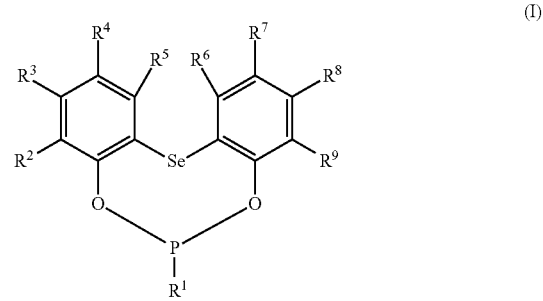

2a
(1.2 eq)

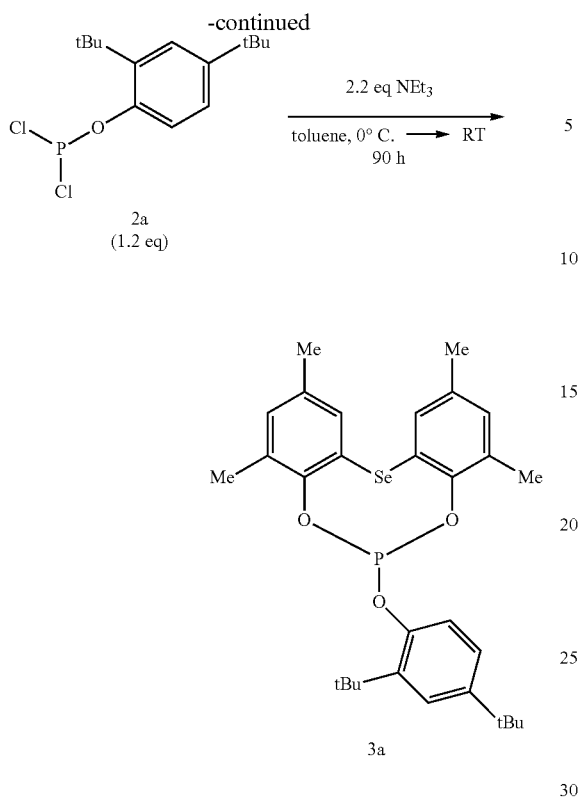

3a

A baked-out 50 ml Schlenk flask under an argon atmosphere was initially charged with 191 mg (0.624 mmol, 1.2 eq, 96% pure) of dichloro(2,4-di-tert-butylphenoxy)phosphite 2a in 5.0 ml of abs. toluene and cooled to 0° C. In a separate 10 ml Schlenk vessel, 168 mg (0.522 mmol, 1.0 eg) of selenodiphenol 1a and 159 µl (116 mg, 1.14 mmol, 2.2 eq) of triethylamine were dissolved in 2.0 ml of abs. toluene. The resulting pale yellow solution was then added dropwise to the initial charge of dichlorophosphite 2a, in the course of which the formation of a colourless precipitate was recorded. The latter was rinsed in with 2.0 ml of abs. toluene and stirred at RT for 48 h. The reaction mixture was filtered for complete removal of the precipitate formed, the solids were washed with 10 ml of abs. toluene, and the solvent was removed under reduced pressure. After crystallization in 10 ml of abs. n-heptane, 191 mg (0.343 mold, 66%, 99.9% in $^{31}$P NMR) of the title compound 3a were obtained as a colourless solid.

IR (ATR): v̂ (cm$^{-1}$)=3425; 2956; 2917; 2865; 1604; 1492; 1464; 1399; 1377; 1360; 1273; 1248; 1208; 1192; 1119; 1084; 1013; 958; 914; 887; 848; 810; 772; 729; 703; 680; 669; 645; 581; 527; 512; 497; 412; $^1$H-NMR (300 MHz, Toluene-d$_8$,): δ (ppm)=7.68-7.46 (m, 2H Ar—CH); 7.40-7.31 (m, 2H Ar—CH); 7.05 (dd, J=8.4 Hz, J=2.5 Hz, 1H Ar—CH); 6.64 (ddd, J=2.3 Hz, J=1.3 Hz, J=0.7 Hz, 2H, Ar—CH); 2.13 (s, 6H, —CH$_3$); 1.97-1.95 (m, 6H, —CH$_3$); 1.65 (s, 9H, —C(CH$_3$)$_3$); 1.31 (s, 9H, —C(CH$_3$)$_3$); $^3$C-NMR (75 MHz, Toluene-d$_8$);

δ (ppm)=152.9 (d, J=5.4 Hz); 150.1 (d, J=4.0 Hz); 145.8; 139.6 (d, J=2.5 Hz); 134.3; 133.8; 133.1; 130.10; 124.4; 124.0; 120.3 (d, J=17.1 Hz); 120.0 (d, J=4.2 Hz); 35.41; 34.57; 31.63; 30.42; 20.16; 17.35; $^{31}$P-NMR (122 MHz, Toluene-d$_8$): δ (ppm)=132.6 (J$_{P—Se}$=62.3 Hz); $^{77}$Se-NMR (57 MHz, Toluene-d$_8$): δ (ppm)=323.0 P$_{Se—P}$=62.3 Hz); C$_{30}$H$_{37}$O$_3$PSe (556.16 g/mol).

18

The invention claimed is:

1. A heterocyclic selenaphosphite compound having a general structure (I)

(I)

where $R^2$, $R^3$, $R^4$, $R^5$, $R^6$, $R^7$, $R^8$ and $R^9$ are each independently selected from: —H, —(C$_1$-C$_{12}$)-alkyl, —O—(C$_1$-C$_{12}$)-alkyl, —(C$_6$-C$_{20}$)-aryl, —O—(C$_6$-C$_{20}$-aryl, -halogen, —OC═O—(C$_1$-C$_{12}$)-alkyl, —S-alkyl,—S-aryl, —COO—(C$_1$-C$_{12}$)-alkyl, —CONH—(C$_1$-C$_{12}$)-alkyl, —CO—(C$_1$-C$_{12}$)-alkyl, —CO—(C$_6$-C$_{20}$)-aryl, —COOH, —SO$_3$H, —CN, or —N[(C$_1$-C$_{12}$)-alkyl]$_2$, where the alkyl groups are each independently linear, branched or cyclic, where the alkyl and aryl groups are each independently unsubstituted or substituted, where each substituted —(C$_1$-C$_{12}$)-alkyl group and substituted —(C$_6$-C$_{20}$)-aryl group has at least one substituent and the at least one substituent in each case is independently selected from —(C$_3$-C$_{12}$)-cycloalkyl, —(C$_3$-C$_{12}$)-heterocycloalkyl, —(C$_6$-C$_{20}$)-aryl, fluorine, chlorine, cyano, formyl, acyl or alkoxycarbonyl, and where —R$^1$ is independently selected from —O—(C$_6$-C$_{20}$)-aryl, —O—(C$_6$-C$_{20}$)-aryl-(C$_1$-C$_{12}$)-alkyl, —O—(C$_6$-C$_{20}$)-aryl-O—(C$_1$-C$_{12}$)-alkyl, —O—(C$_6$-C$_{20}$)-aryl-(C$_6$-C$_{20}$)-aryl, —O—(C$_6$-C$_{20}$)-aryl-O—(C$_6$-C$_{20}$)-aryl, —O—(C$_1$-C$_{12}$)-alkyl, —O—(C$_1$-C$_{12}$)-alkyl-O—(C$_1$-C$_{12}$)-alkyl, —O—(C$_1$-C$_{12}$)-alkyl-(C$_6$-C$_{20}$)-aryl, or —O—(C$_3$-C$_{12}$)-cycloalkyl, where the alkyl groups are linear, branched or cyclic, Where the alkyl and aryl groups mentioned are each independently unsubstituted or substituted, each substituted —(C$_6$-C$_{20}$)-aryl group has at least one or more than one substituent, and where the substituents on each aryl group are independently selected from: —O—(C$_1$-C$_{12}$)-alkyl, —(C$_1$-C$_{12}$)-alkyl-O—(C$_1$-C$_{12}$)-alkyl, —(C$_1$-C$_{12}$)-alkyl, —O—(C$_6$-C$_{20}$)-aryl, —O—(C$_1$-C$_{12}$-alkyl-O—(C$_1$-C$_{12}$)-alkyl, —O—(C$_6$-C$_{20}$)-aryl-O—(C$_1$-C$_{12}$)-alkyl, —(C$_3$-C$_{12}$)-cycloalkyl, —(C$_3$-C$_{12}$)-heterocycloalkyl, —(C$_6$-C$_{20}$)-aryl, cyano, -halogen, —OCOO—(C$_1$-C$_{12}$)-alkyl, or —N[(C$_1$-C$_{12}$)-alkyl]$_2$.

2. The compound according to claim 1, wherein in the heterocyclic selenaphosphite of the general structure (I), R$^1$ is selected from the structures (II), (III), (IV), (V), (VI), (VII), (VIII), (IX) and (X)

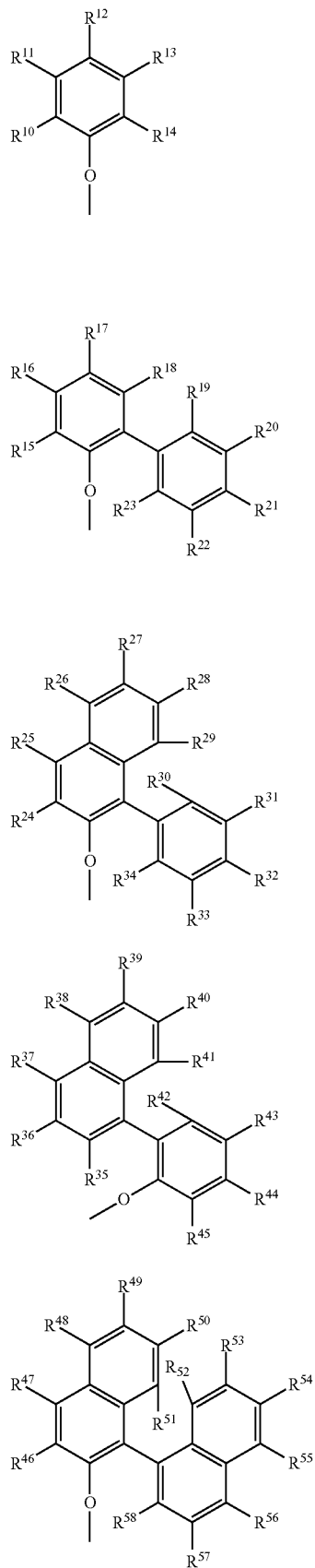

where the radicals $R^{10}$, $R^{11}$, $R^{12}$, $R^{13}$, $R^{14}$ in the structure (II), $R^{15}$, $R^{16}$, $R^{17}$, $R^{18}$, $R^{19}$, $R^{20}$, $R^{21}$, $R^{22}$ and $R^{23}$ in structure (III), $R^{24}$, $R^{25}$, $R^{26}$, $R^{27}$, $R^{28}$, $R^{29}$, $R^{30}$, $R^{31}$, $R^{32}$, $R^{33}$ and $R^{34}$ in structure (IV), $R^{35}$, $R^{36}$, $R^{37}$, $R^{38}$, $R^{39}$, $R^{40}$, $R^{41}$, $R^{42}$, $R^{43}$, $R^{44}$ and $R^{45}$ in structure (V), $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$ and $R^{58}$ in structure (VI), $R^{59}$, $R^{60}$, $R^{61}$, $R^{62}$, $R^{63}$, $R^{64}$ and $R^{65}$ in structure (VII), and $R^{66}$, $R^{67}$, $R^{68}$, $R^{69}$, $R^{70}$, $R^{71}$, $R^{72}$, $R^{73}$ and $R^{74}$ in structure (VIII), in each structure are each independently selected from: —H, —($C_1$-$C_{12}$)-alkyl, 13 O—($C_1$-$C_{12}$)-alkyl, —($C_6$-$C_{20}$)-aryl, —O—($C_6$-$C_{20}$)-aryl, or -halogen, where the alkyl and aryl groups are each independently unsubstituted or substituted, where each substituted —($C_1$-$C_{12}$)-alkyl group and each substituted —($C_6$-$C_{20}$)-aryl group has at least one substituent and the at least one substituent in each case is independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, where, in the structures (III), (IV), (V) and (VI), $R^{23}$, $R^{34}$, $R^{45}$, $R^{58}$ are each independently additionally selected from —O—X with X=protecting group, where the protecting group X is selected from —($C_1$-$C_{12}$)-alkyl-O—($C_1$-$C_{12}$)-alkyl, —($C_6$-$C_{20}$)-aryl-O—($C_1$-$C_{12}$)-alkyl, or —COO—($C_1$-$C_{12}$)-alkyl.

3. The compound according to claim 1, wherein the heterocyclic selenaphosphite has the general structure (Ia)

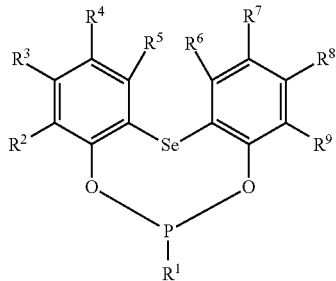
(Ia)

where $R^2$, $R^3$, $R^4$, $R^5$, $R^6$, $R^7$, $R^8$ and $R^9$ are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen, and —$R^1$ in the heterocyclic selenaphosphite of the general structure (Ia) is independently selected from the structures (II), (III), (IV), (V), (VI), (VII), (VIII), (IX) and (X)

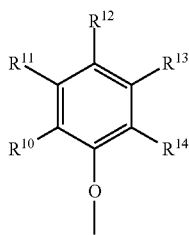
(II)

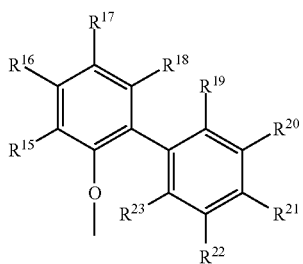
(III)

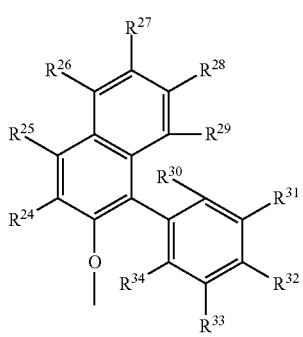
(IV)

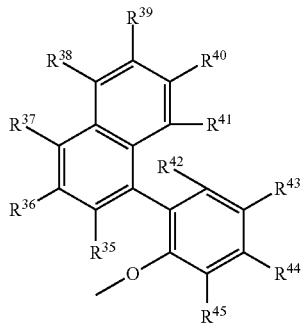
(V)

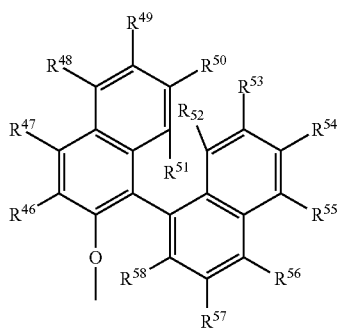
(VI)

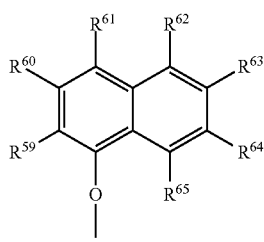
(VII)

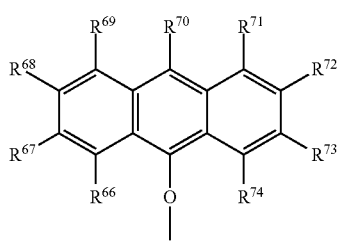
(VIII)

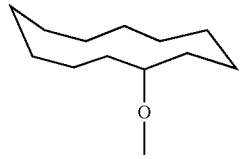
(IX)

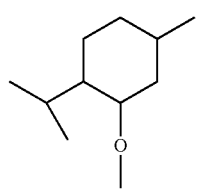
(X)

where the radicals
$R^{10}$, $R^{11}$, $R^{12}$, $R^{13}$, $R^{14}$ in the structure (II),
$R^{15}$, $R^{16}$, $R^{17}$, $R^{18}$, $R^{19}$, $R^{20}$, $R^{21}$ and $R^{22}$ in structure (III),
$R^{24}$, $R^{25}$, $R^{26}$, $R^{27}$, $R^{28}$, $R^{29}$, $R^{30}$, $R^{31}$, $R^{32}$ and $R^{33}$ in structure (IV), $R^{35}$, $R^{36}$, $R^{37}$, $R^{38}$, $R^{39}$, $R^{40}$, $R^{41}$, $R^{42}$, $R^{43}$ and $R^{44}$ in structure V, $R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ in structure (VI), $R^{59}$, $R^{60}$, $R^{61}$, $R^{62}$, $R^{63}$, $R^{64}$ and $R^{65}$ in structure (VII), and $R^{66}$, $R^{67}$, $R^{68}$, $R^{69}$, $R^{70}$, $R^{71}$, $R^{72}$, $R^{73}$ and $R^{74}$ in structure (VIII), in each structure are each independently selected from: —H, —($C_1$-$C_{12}$)-alkyl, —O—($C_1$-$C_{12}$)-alkyl, or -halogen, and where, in each case independently, in addition to the aforementioned groups in the structures (III), (IV), (V) and (VI), $R^{23}$, $R^{34}$, $R^{45}$, $R^{58}$ are each independently selected from —H, —($C_1$-$C_{12}$)-alkyl, -halogen and —O—X with X=protecting group, where the protecting group X is selected from —($C_1$-$C_{12}$)-alkyl, —($C_1$-$C_{12}$)-alkyl-O—($C_1$-$C_{12}$)-alkyl, —($C_6$-$C_{20}$)-aryl-O—($C_1$-$C_{12}$)-alkyl, or —COO—($C_1$-$C_{12}$)-alkyl.

4. The compound according to claim 3, wherein the heterocyclic selenaphosphite of the general structure (Ia) is selected from a compound of structure (Ib) with $R^1$ corresponding to the definition immediately above

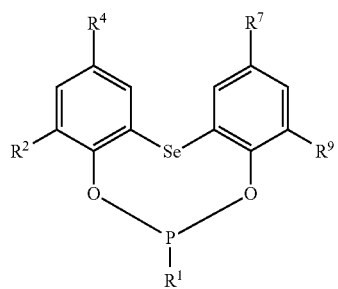

(Ib)

where $R^2$, $R^4$, $R^7$ and $R^9$ are each independently selected from:

—($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen, where the alkyl groups are each independently linear, branched or cyclic.

5. The compound according to claim 1, wherein in the heterocyclic selenaphosphite of the general structure (I)

$R^2$, $R^3$, $R^4$, $R^5$, $R^6$, $R^7$, $R^8$ and $R^9$ are each independently selected from: —H, —($C_1$-$C_{12}$)-alkyl, or —O—($C_1$-$C_{12}$)-alkyl, and —$R^1$ in the heterocyclic selenaphosphite of the general structure (I) is independently selected from the structures (II), (III), (IV), (V), (VI), (VII), (VIII), (IX) and (X):

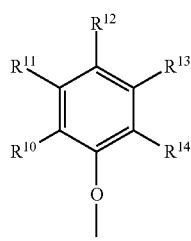

(II)

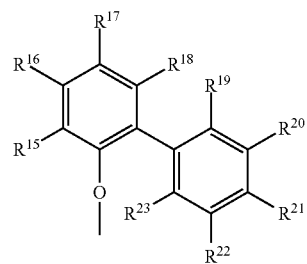

(III)

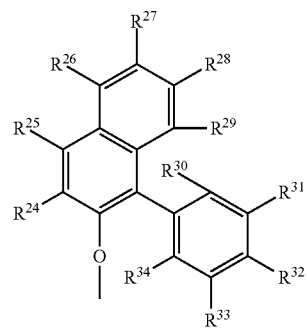

(IV)

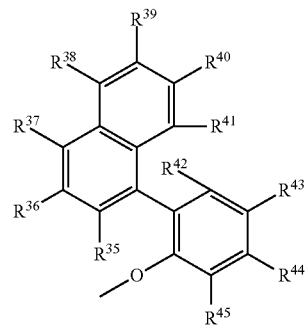

(V)

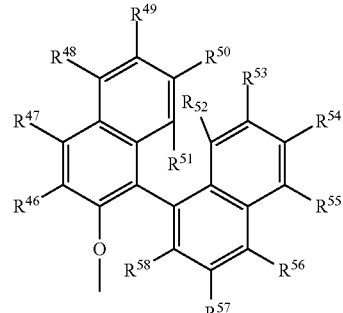

(VI)

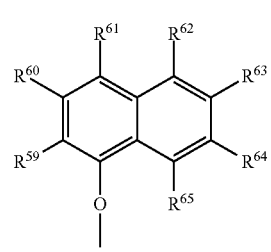

(VII)

-continued

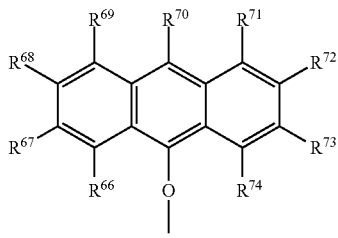
(VIII)

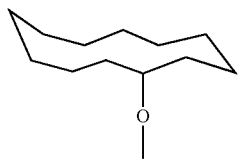
(IX)

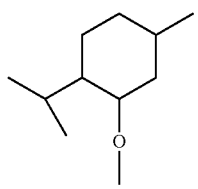
(X)

where the radicals
$R^{10}, R^{11}, R^{12}, R^{13}, R^{14}$ in the structure (II),
$R^{15}, R^{16}, R^{17}, R^{18}, R^{19}, R^{20}, R^{21}$ and $R^{22}$ in structure (III),
$R^{24}, R^{25}, R^{26}, R^{27}, R^{28}, R^{29}, R^{30}, R^{31}, R^{32}$ and $R^{33}$ in structure (IV),
$R^{35}, R^{36}, R^{37}, R^{38}, R^{39}, R^{40}, R^{41}, R^{42}, R^{43}$ and $R^{44}$ in structure (V),
$R^{46}, R^{47}, R^{48}, R^{49}, R^{50}, R^{51}, R^{52}, R^{53}, R^{54}, R^{55}, R^{56}$ and $R^{57}$ in structure (VI),
$R^{59}, R^{60}, R^{61}, R^{62}, R^{63}, R^{64}$ and $R^{65}$ in structure (VII), and
$R^{66}, R^{67}, R^{68}, R^{69}, R^{70}, R^{71}, R^{72}, R^{73}$ and $R^{74}$ in structure (VIII),
in each structure are each independently selected from:
—H, —$(C_1-C_{12})$-alkyl, or
—O—$(C_1-C_{12})$-alkyl, and where in each case independently, in addition to the aforementioned groups in the structures (III), (IV), (V) and (VI), $R^{23}, R^{34}, R^{45}, R^{58}$ are each independently selected from —H and —O—X with X=protecting group, where the protecting group X is selected from —$(C_1-C_{12})$-alkyl, —$(C_1-C_{12})$-alkyl-O—$(C_1-C_{12})$-alkyl, —$(C_6-C_{20})$-aryl-O—$(C_1-C_{12})$-alkyl, or —COO—$(C_1-C_{12})$-alkyl.

6. A rhodium hydroformylation catalyst comprising: the compound according to claim 1.

7. A process for preparing at least one heterocyclic selenaphosphite of the general structure (I)

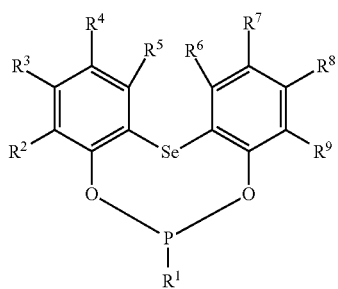
(I)

where $R^2, R^3, R^4, R^5, R^6, R^7, R^8$ and $R^9$ are each independently selected from: —H, —$(C_1-C_{12})$-alkyl, —O—$(C_1-C_{12})$-alkyl, —$(C_6-C_{20})$-aryl, —O—$(C_6-C_{20})$-aryl, -halogen, —OC=O—$(C_1-C_{12})$-alkyl, —S-alkyl, —S-aryl, —COO—$(C_1-C_{12})$-alkyl, —CONH—$(C_1-C_{12})$-alkyl, —CO—$(C_1-C_{12})$-alkyl, —CO—$(C_6-C_{20})$-aryl, —COOH, —SO$_3$H, —CN, or —N[$(C_1-C_{12})$-alkyl]$_2$, where the alkyl groups are each independently linear, brandied or cyclic, Where the alkyl and aryl groups are each independently unsubstituted cr substituted, where each substituted —$(C_1-C_{12})$-alkyl group and substituted —$(C_6-C_{20})$-aryl group has at least, one substituent and the at least one substituent in each case is independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl, and where —$R^1$ is independently selected from
—O—$(C_6-C_{20})$-aryl, —O—$(C_6-C_{20})$-aryl-$(C_1-C_{12})$-alkyl, —O—$(C_6-C_{20})$-aryl-O—$(C_1-C_{12})$-alkyl,
—O—$(C_6-C_{20})$-aryl-$(C_6-C_{20})$-aryl, —O—$(C_6-C_{20})$-aryl-O—$(C_6-C_{20})$-aryl, —O—$(C_1-C_{12})$-alkyl,
—O—$(C_1-C_{12})$-alkyl-O—$(C_1-C_{12})$- alkyl, —O—$(C_1-C_{12})$-alkyl-$(C_6-C_{20})$-aryl, or
—O—$(C_3-C_{12})$-cycloalkyl, where alkyl in each case is independently linear, branched or cyclic, where the alkyl and aryl groups mentioned are each independently unsubstituted or substituted, each substituted —$(C_6-C_{20})$-aryl group has at least one or more than one substituent; and
where the substituents on each aryl group are independently selected from: —O—$(C_1-C_{12})$-alkyl, —$(C_1-C_{12})$-alkyl-O—$(C_1-C_{12})$-alkyl, —$(C_1-C_{12})$-alkyl, —O—$(C_6-C_{20})$-aryl, —O—$(C_1-C_{12})$-alkyl-O—$(C_1-C_{12})$-alkyl, —O—$(C_6-C_{20})$-aryl-O—$(C_1-C_{12})$-alkyl, —$(C_3-C_{12})$-cycloalkyl, —$(C_3-C_{12})$heterocycloalkyl, —$(C_6-C_{20})$-aryl, cyano, -halogen, —O—COO—$(C_1-C_{12})$-alkyl, or —N[$(C_1-C_{12})$-alkyl]$_2$,
comprising at least the process step of
(i) reacting a selenodiaryl of the general structure (XI)

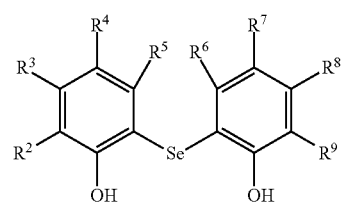
(XI)

where $R^2, R^3, R^4, R^5, R^6, R^7, R^8$ and $R^9$ are each independently selected from: —H, —$(C_1-C_{12})$-alkyl, —O—$(C_1-C_{12})$-alkyl, —$(C_6-C_{20})$-aryl, —O—$(C_6-C_{20})$-aryl, -halogen, —OC=O—$(C_1-C_{12})$-alkyl, —S-alkyl, —S-aryl, —COO—$(C_1-C_{12})$-alkyl, —CONH—$(C_1-C_{12})$-alkyl, —CO—$(C_1-C_{12})$-alkyl, —CO—$(C_6-C_{20})$-aryl, —COOH, —SO$_3$H, —CN, or —N[$(C_1-C_{12})$-alkyl]$_2$, where the alkyl groups are each independently linear, branched or cyclic, where the alkyl and aryl groups are each independently unsubstituted or substituted, where each substituted —$(C_1-C_{12})$-alkyl group and substituted —$(C_6-C_{20})$-aryl group has at least one substituent and the at least one substituent in each case is independently selected from —$(C_3-C_{12})$-cycloalkyl, —$(C_3-C_{12})$- heterocycloalkyl, —($C_6$-$C_{20}$)-aryl, fluorine, chlorine, cyano, formyl, acyl or alkoxycarbonyl, (ii) with a dihalophosphite compound $R^1P(Hal)_2$, where Hal is selected from fluorine, chlorine, bromine, or iodine, where $R^1$ corresponds to the definition immediately above, (iii) and obtaining at least one selenaphosphite of the general structure (I).

8. The process according to claim 7, wherein the selenodiaryl of the general structure (XI) corresponds to a compound of the structure (XIa)

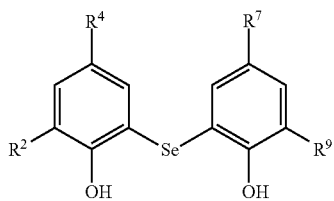

(XIa)

where $R^2$, $R^4$, $R^7$ and $R^9$ are each independently selected from:

—($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen, where the alkyl groups are each independently linear, branched or cyclic.

9. The process according to claim 7, wherein in the dihalophosphite compound $R^1P(Hal)_2$ Hal is selected from fluorine, chlorine, bromine, or iodine, and $R^1$ is independently selected from the structures (II), (III), (IV), (V), (VI), (VII), (VIII), (IX) and (X)

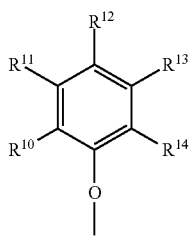

(II)

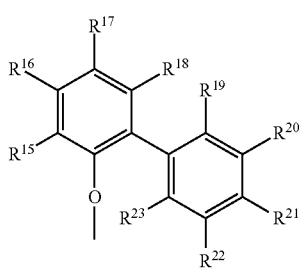

(III)

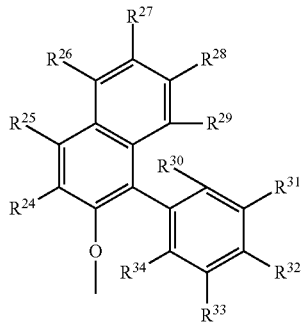

(IV)

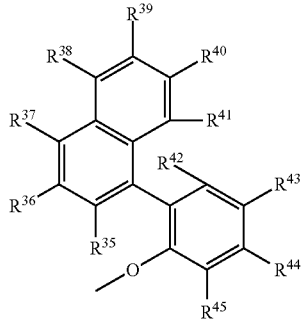

(V)

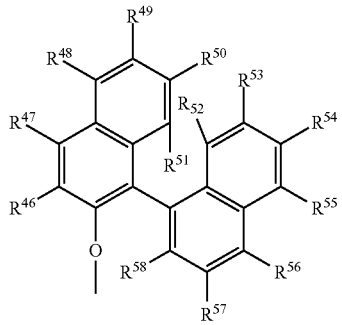

(VI)

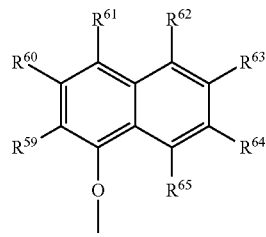

(VII)

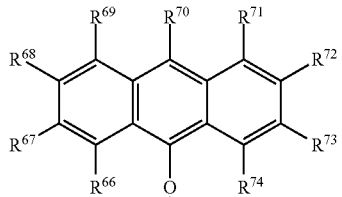

(VIII)

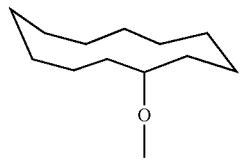

(IX)

-continued

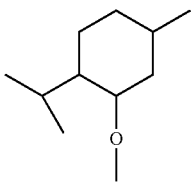

(X)

where the radicals
$R^{10}$, $R^{11}$, $R^{12}$, $R^{13}$, $R^{14}$ in the structure (II),
$R^{15}$, $R^{16}$, $R^{17}$, $R^{18}$, $R^{19}$, $R^{20}$, $R^{21}$ and $R^{22}$ in structure (III),
$R^{24}$, $R^{25}$, $R^{26}$, $R^{27}$, $R^{28}$, $R^{29}$, $R^{30}$, $R^{31}$, $R^{32}$ and $R^{33}$ in structure (IV),
$R^{35}$, $R^{36}$, $R^{37}$, $R^{38}$, $R^{39}$, $R^{40}$, $R^{41}$, $R^{42}$, $R^{43}$ and $R^{44}$ in structure (V),
$R^{46}$, $R^{47}$, $R^{48}$, $R^{49}$, $R^{50}$, $R^{51}$, $R^{52}$, $R^{53}$, $R^{54}$, $R^{55}$, $R^{56}$ and $R^{57}$ in structure (VI),
$R^{59}$, $R^{60}$, $R^{61}$, $R^{62}$, $R^{63}$, $R^{64}$ and $R^{65}$ in structure (VII), and $R^{66}$, $R^{67}$, $R^{68}$, $R^{69}$, $R^{70}$, $R^{71}$, $R^{72}$, $R^{73}$ and $R^{74}$ in structure (VIII),
are each independently selected from: —H, —($C_1$-$C_{12}$)-alkyl, —O—($C_1$-$C_{12}$)-alkyl, or -halogen, and
where, in each case independently, in addition to the aforementioned groups in the structures (III), (IV), (V) and (VI), $R^{23}$, $R^{34}$, $R^{45}$, $R^{58}$ are each independently selected from —H, —($C_1$-$C_{12}$)-alkyl, -halogen and —O—X with X=protecting group, where the protecting group X is selected from —($C_1$-$C_{12}$)-alkyl, —($C_1$-$C_{12}$)-alkyl-O—($C_1$-$C_{12}$)-alkyl, —($C_6$-$C_{20}$)-aryl-O—($C_1$-$C_{12}$)-alkyl, or —COO—($C_1$-$C_{12}$)-alkyl.

10. The process according to claim 7, wherein (i) the reaction is effected in the presence of a base.

11. The process according to claim 7, wherein the selenodiaryl of the general structure (XI) is reacted with $R^1P(Hal)_2$ in a molar ratio of 10:1 to 1:10.

12. The process according to claim 7, wherein $R^1P(Hal)_2$ is $R^1PCl_2$ or $R^1PBr_2$.

13. The process according to claim 7, wherein (i) the reaction is effected in a temperature range from −45 to 80° C.

14. The process of claim 10, wherein (i) the reaction is effected in the presence of an amine base or pyridine base.

15. The process of claim 10, wherein (i) the reaction is effected in the presence of an alkylamine.

16. The process of claim 11, wherein the selenodiaryl of the general structure (XI) is reacted with $R^1P(Hal)_2$ in a molar ratio of 2:1 to 1:2.

17. The process of claim 13, wherein (i) the reaction is effected in the temperature range from −15 to 30° C.

* * * * *